US011103189B2

(12) United States Patent
Shute et al.

(10) Patent No.: US 11,103,189 B2
(45) Date of Patent: Aug. 31, 2021

(54) MULTICHANNEL HEART SOUND DETECTION

(71) Applicant: Cardiac Pacemakers, Inc., St. Paul, MN (US)

(72) Inventors: Jonathan Bennett Shute, Minnetonka, MN (US); Bin Mi, Arden Hills, MN (US); Qi An, Blaine, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 293 days.

(21) Appl. No.: 16/113,144

(22) Filed: Aug. 27, 2018

(65) Prior Publication Data

US 2019/0083041 A1 Mar. 21, 2019

Related U.S. Application Data

(60) Provisional application No. 62/561,137, filed on Sep. 20, 2017.

(51) Int. Cl.
*A61B 5/00* (2006.01)
*A61B 7/04* (2006.01)
*A61N 1/365* (2006.01)

(52) U.S. Cl.
CPC .............. *A61B 5/7214* (2013.01); *A61B 7/04* (2013.01); *A61N 1/36578* (2013.01); *A61B 5/726* (2013.01); *A61B 5/7207* (2013.01); *A61B 2562/0204* (2013.01); *A61B 2562/0219* (2013.01)

(58) Field of Classification Search
CPC . A61B 5/7214; A61B 7/04; A61B 2562/0204; A61B 2562/0219; A61B 5/7207; A61B 5/726; A61N 1/36578
See application file for complete search history.

(56) References Cited

U.S. PATENT DOCUMENTS 4,951,678 A * 8/1990 Joseph .................... A61B 7/023
600/484

* cited by examiner

*Primary Examiner* — Mark W. Bockelman
(74) *Attorney, Agent, or Firm* — Shwegman Lundberg & Woessner, P.A.

(57) ABSTRACT

This document discusses, among other things, systems and methods to produce a combined heart sound signal of a patient using a first signal including heart sound information over a first physiologic interval and a second signal including heart sound information over the first physiologic interval.

16 Claims, 5 Drawing Sheets

MULTICHANNEL HEART SOUND DETECTION

CLAIM OF PRIORITY

This application claims the benefit of priority under 35 U.S.C. § 119(e) of U.S. Provisional Patent Application Ser. No. 62/561,137, filed on Sep. 20, 2017, which is herein incorporated by reference in its entirety.

TECHNICAL FIELD

This document relates generally to medical devices, and more particularly, but not by way of limitation, to systems, devices, and methods to detect heart sounds.

BACKGROUND

Implantable medical devices, such as cardiac rhythm management (CRM) devices, can be used to monitor, detect, or treat various cardiac conditions that can result in a reduced ability of a heart to sufficiently deliver blood to a body. In some cases, heart conditions may lead to rapid, irregular, or inefficient heart contractions. To alleviate one or more of these conditions, various medical devices can be implanted in a patient's body to monitor heart activity or to provide electrical stimulation to optimize or control contractions of the heart.

Overview

Traditional cardiac rhythm management (CRM) devices, such as pacemakers or defibrillators, include subcutaneous devices implanted in a chest of a patient, having one or more leads to position one or more electrodes or other sensors at various locations in the heart, such as in one or more of the atria or ventricles. In certain examples, the one or more leads can include a pressure sensor positioned in the heart and coupled to the CRM device through a conductor in the lead. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

For example, the CRM device or the one or more leads can include an acoustic sensor, such as an accelerometer, a microphone, or one or more other acoustic sensors configured to detect body sounds from a patient, such as cardiac murmurs, respiratory sounds, heart sounds, mitral regurgitation, mitral stenosis, or other body sounds. The body sounds, or other physiologic information, can be used to diagnose one or more physiologic conditions, provide an alert, or to control one or more therapies.

Leadless devices, such as implantable cardiac monitors, leadless cardiac pacemakers (LCP), insertable cardiac monitors (ICM), etc., and external devices, such as wearable remote patient monitors, etc., have developed that can detect physiologic information from, and in certain examples, provide one or more therapies or stimulation to the heart, without traditional lead or implantable CRM device complications. Such leadless and wearable devices are typically small, self-contained devices (e.g., smaller than traditional implantable CRM devices), in certain examples, having even more limited power and processing capabilities than a traditional CRM device.

This document discusses, among other things, apparatus, systems, or methods to produce a combined heart sound signal by using one or more signals containing heart sound information. In some examples, the combined heart sound signal can be created using a single signal and in other examples, the combined heart sound signal can be created using multiple signals.

An example system can include a heart sound input circuit configured to receive a first signal including heart sound information over a first physiologic interval and a second signal including heart sound information over the first physiologic interval. The first physiologic interval can include at least a portion of a cardiac cycle. Also, the system can include a combination circuit configured to produce a combined heart sound signal over the first physiologic interval using the first and second signals.

An example (e.g., "Example 1") of subject matter (e.g., a system) may include a system comprising: a heart sound input circuit configured to: receive a first signal including heart sound information over a first physiologic interval; and receive a second signal including heart sound information over the first physiologic interval; and a combination circuit configured to produce a combined heart sound signal over the first physiologic interval using the first and second signals.

In Example 2, the subject matter of Example 1 may optionally be configured such that the combination circuit is configured to align the first and second signals using a covariance of the first and second signals, and to produce the combined heart sound signal using the aligned first and second signals.

In Example 3, the subject matter of any one or more of Examples 1-2 may optionally be configured such that the first signal includes heart sound information detected along a first axis and the second signal includes heart sound information detected along a second axis, different from the first axis.

In Example 4, the subject matter of any one or more of Examples 1-3 may optionally be configured such that the combination circuit is configured to produce the combined heart sound signal using the first and second signals without reference to an electrical signal of the heart, and wherein the first physiologic interval includes at least a portion of a cardiac cycle.

In Example 5, the subject matter of any one or more of Examples 1-4 may optionally be configured such that the heart sound input circuit is configured to receive a third signal including heart sound information over the first physiologic interval, and wherein the combination circuit is configured to produce the combined heart sound signal using the first, second, and third signals.

In Example 6, the subject matter of any one or more of Examples 1-5 may optionally include a heart sound sensor configured to detect heart sound information over the first physiologic interval, to produce the first signal as a function of heart sound information detected over the first physiologic interval, and to produce the second signal as a function of heart sound information detected over the first physiologic interval.

In Example 7, the subject matter of any one or more of Examples 1-6 may optionally be configured such that the heart sound input circuit is configured to receive a third signal including heart sound information over the first physiologic interval, wherein the combination circuit is configured to produce the combined heart sound signal using the first, second, and third signals, and wherein the heart sound sensor is configured to produce the third signal as a function of heart sound information detected over the first physiologic interval.

Example 8 is a method comprising: receiving a first signal including heart sound information over a first physiologic interval using a heart sound input circuit; receiving a second signal including heart sound information over the first physiologic interval using the heart sound input circuit; and producing, using a combination circuit, a combined heart sound signal over the first physiologic interval using the first and second signals.

In Example 9, the subject matter of Example 8 may optionally be configured such that producing the combined heart sound signal is performed without reference to an electrical signal of the heart, and wherein the first physiologic interval includes at least a portion of a cardiac cycle.

In Example 10, the subject matter of any one or more of Examples 8-9 may optionally be configured such that producing the combined heart sound signal includes aligning the first and second signals using a covariance of the first and second signals, and producing the combined heart sound signal using the aligned first and second signals.

In Example 11, the subject matter of any one or more of Examples 8-10 may optionally be configured such that the first signal includes heart sound information detected along a first axis and the second signal includes heart sound information detected along a second axis, different from the first axis.

In Example 12, the subject matter of any one or more of Examples 8-11 may optionally include providing the first signal and the second signal using a multi-axis heart sound sensor.

In Example 13, the subject matter of any one or more of Examples 8-12 may optionally include receiving a third signal including heart sound information over the first physiologic interval using the heart sound input circuit, wherein producing the combined heart sound signal over the first physiologic interval includes using the first, second, and third signals.

In Example 14, the subject matter of any one or more of Examples 8-13 may optionally include detecting heart sound information over the first physiologic interval using a heart sound sensor; and producing the first signal as a function of heart sound information detected over the first physiologic interval and the second signal as a function of heart sound information detected over the first physiologic interval using the heart sound sensor.

In Example 15, the subject matter of any one or more of Examples 8-14 may optionally include receiving a third signal including heart sound information over the first physiologic interval using the heart sound input circuit, wherein producing the combined heart sound signal over the first physiologic interval includes using the first, second, and third signals; and producing the third signal as a function of heart sound information detected over the first physiologic interval using the heart sound sensor.

Example 16 is a system comprising: a heart sound input circuit configured to: receive a first signal including heart sound information over a first physiologic interval; and receive a second signal including heart sound information over the first physiologic interval; and a combination circuit configured to produce a combined heart sound signal over the first physiologic interval using the first and second signals.

In Example 17, the subject matter of Example 16 may optionally be configured such that the combination circuit is configured to align the first and second signals using a covariance of the first and second signals, and to produce the combined heart sound signal using the aligned first and second signals.

In Example 18, the subject matter of any one or more of Examples 16-17 may optionally be configured such that the combination circuit is configured to produce the combined heart sound signal using the first and second signals without reference to an electrical signal of the heart, and wherein the first physiologic interval includes at least a portion of a cardiac cycle.

In Example 19, the subject matter of any one or more of Examples 16-18 may optionally be configured such that the first signal includes heart sound information detected along a first axis and the second signal includes heart sound information detected along a second axis, different from the first axis.

In Example 20, the subject matter of any one or more of Examples 16-19 may optionally be configured such that the heart sound input circuit is configured to receive a third signal including heart sound information over the first physiologic interval, and wherein the combination circuit is configured to produce the combined heart sound signal using the first, second, and third signals.

In Example 21, the subject matter of any one or more of Examples 16-20 may optionally include a heart sound sensor configured to detect heart sound information over the first physiologic interval, to produce the first signal as a function of heart sound information detected over the first physiologic interval, and to produce the second signal as a function of heart sound information detected over the first physiologic interval.

In Example 22, the subject matter of Example 21 may optionally be configured such that the heart sound input circuit is configured to receive a third signal including heart sound information over the first physiologic interval, wherein the combination circuit is configured to produce the combined heart sound signal using the first, second, and third signals, and wherein the heart sound sensor is configured to produce the third signal as a function of heart sound information detected over the first physiologic interval.

Example 23 is a method comprising: receiving a first signal including heart sound information over a first physiologic interval using a heart sound input circuit; receiving a second signal including heart sound information over the first physiologic interval using the heart sound input circuit; and producing, using a combination circuit, a combined heart sound signal over the first physiologic interval using the first and second signals.

In Example 24, the subject matter of Example 23 may optionally be configured such that producing the combined heart sound signal is performed without reference to an electrical signal of the heart, and wherein the first physiologic interval includes at least a portion of a cardiac cycle.

In Example 25, the subject matter of any one or more of Examples 23-24 may optionally be configured such that producing the combined heart sound signal includes aligning the first and second signals using a covariance of the first and second signals, and producing the combined heart sound signal using the aligned first and second signals.

In Example 26, the subject matter of any one or more of Examples 23-25 may optionally be configured such that the first signal includes heart sound information detected along a first axis and the second signal includes heart sound information detected along a second axis, different from the first axis.

In Example 27, the subject matter of Example 26 may optionally include providing the first signal and the second signal using a multi-axis heart sound sensor.

In Example 28, the subject matter of any one or more of Examples 23-27 may optionally include receiving a third signal including heart sound information over the first physiologic interval using the heart sound input circuit, wherein producing the combined heart sound signal over the first physiologic interval includes using the first, second, and third signals.

In Example 29, the subject matter of any one or more of Examples 23-28 may optionally include detecting heart sound information over the first physiologic interval using a heart sound sensor; and producing the first signal as a function of heart sound information detected over the first physiologic interval and the second signal as a function of heart sound information detected over the first physiologic interval using the heart sound sensor.

In Example 30, the subject matter of Example 29 may optionally include receiving a third signal including heart sound information over the first physiologic interval using the heart sound input circuit, wherein producing the combined heart sound signal over the first physiologic interval includes using the first, second, and third signals; and producing the third signal as a function of heart sound information detected over the first physiologic interval using the heart sound sensor.

Example 31 is a system comprising: a heart sound input circuit configured to receive a single signal including heart sound information and to provide a first signal including a first portion of the heart sound information and a second signal including a different second portion of the heart sound information; and a combination circuit configured to produce a combined heart sound signal over the first physiologic interval using the first and second signals.

In Example 32, the subject matter of Example 31 may optionally be configured such that the heart sound input circuit is configured to split the single signal into the first and second signals.

In Example 33, the subject matter of Example 32 may optionally be configured such that the heart sound input circuit is configured to filter the single signal into the first and second signals, the first signal having a different range of frequencies than the second signal.

In Example 34, the subject matter of any one or more of Examples 31-33 may optionally be configured such that the combination circuit is configured to produce the combined heart sound signal using the first and second signals without reference to an electrical signal of the heart.

In Example 35, the subject matter of any one or more of Examples 31-34 may optionally be configured such that the combination circuit is configured to align the first and second signals using a covariance of the first and second signals, and to produce the combined heart sound signal using the aligned first and second signals.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Heart sounds are recurring mechanical signals associated with cardiac vibrations from and blood flow through the heart with each cardiac cycle, and can be separated and classified according to activity associated with the vibrations and blood flow. The first heart sound (S1) is the vibrational sound made by the heart during closure of the atrioventricular (AV) valves. The second heart sound (S2) is the beginning of diastole, and is made by the aortic and pulmonary valves. The third and fourth heart sounds (S3, S4) are related to filling pressures of the left ventricle during diastole.

Heart sounds can be sensed or detected by sensors, such as accelerometers, in close proximity to a heart. However, the sensors used to detect heart sounds often detect other vibrations, resulting in signal noise. The noise can be caused by, among other things, postural changes, body movement, changes in orientation relative to the direction of gravity, etc., to reduce signal noise in a signal including heart sound information, multiple instance windows of heart sounds can be averaged together, where the instance window can be determined using an R wave or one or more other markers or fiducials of an ECG signal. However, error in the R wave or other marker or fiducial of the ECG signal can distort a resulting averaged heart sound. The present inventors have recognized, among other things, that multiple signals, in certain examples, without reference to an electrical signal of the heart, can be used to create a combined heart sound signal with a relatively low signal-to-noise ratio that is not susceptible to errors in the R wave or one or more other markers or fiducials of an ECG signal.

In some examples, the signals can be analyzed, such as by calculating covariance of the signals, to detect one or more fiducials or other markers. The detected fiducials or markers can be used to align the signals for combination, such as by averaging or otherwise combining the signals to produce a combined heart sound signal. In other examples, the combined heart sound signal can be analyzed over multiple physiologic intervals to detect one or more fiducials or other markers to produce one or more other combination heart sound signals across multiple physiologic intervals.

By eliminating the need for R wave detection, components required to produce the R wave signal can be eliminated, allowing the device to be manufactured in a smaller form factor and at a lower cost. Additionally, by eliminating the need for R wave detection, efficiency and therefore battery life can be improved. Along these lines, because the device can produce a signal with reduced noise, the amount of filtering required can be reduced, and in some instances, a required processing power can be reduced, further increasing operating efficiency and improving battery life.

Figure 1A:
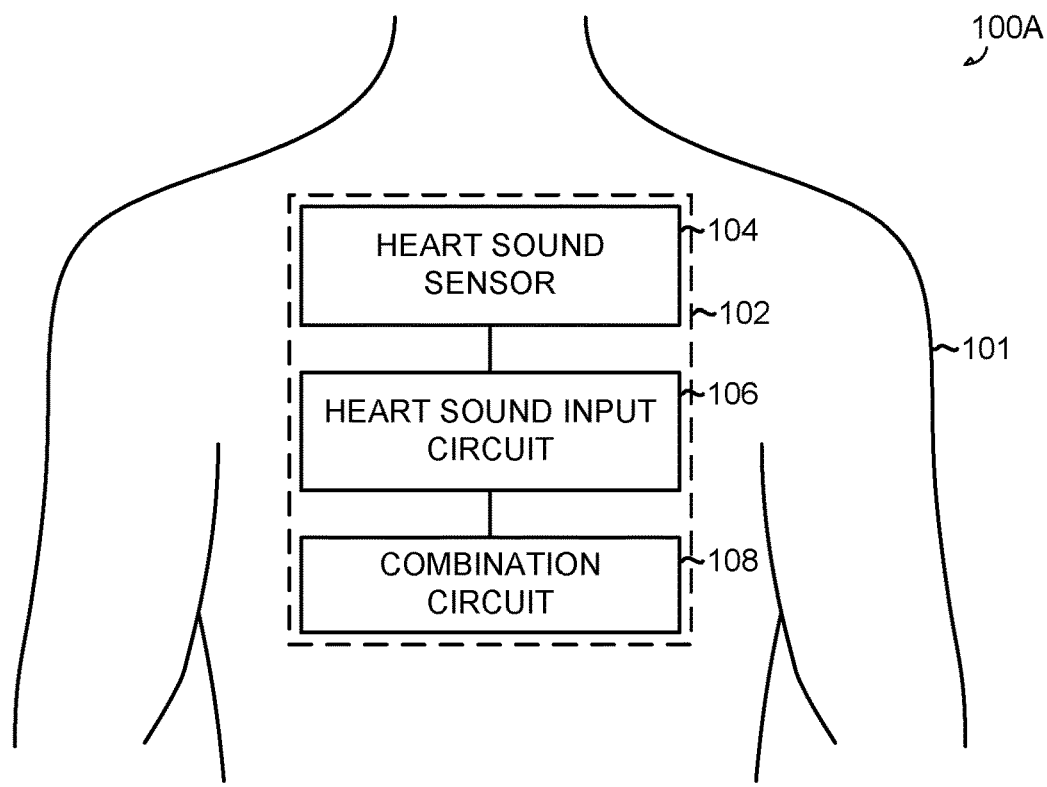
FIG. 1A-1B illustrate schematic views of example cardiac monitoring systems.

FIG. 1A illustrates a schematic view of an example system 100A including device 102, such as a leadless devices, such as implantable cardiac monitors, leadless cardiac pacemakers, insertable cardiac monitors, etc., and external devices, such as wearable remote patient monitor. In other examples, device 102 can be one or more other management or therapy devices configured to detect heart sound information of patient 101. In an example, device 102 can include heart sound sensor 104 configured to receive heart sound information of a heart of patient 101. Heart sound input circuit 106 can be configured to receive signals including heart sound information from heart sound sensor 104. Combination circuit 108 can be configured to produce a combined heart sound signal using the signals received from heart sound input circuit 106.

In some examples, heart sound sensor 104 can be a sensor configured to detect heart sound information along one or more axes during physiologic intervals that include at least a portion of a cardiac cycle. Heart sensor 104 can be further configured to produce one or more signals as a function of the detected heart sound information. In some examples, heart sound sensor 104 can be an accelerometer, microphone, or other transducer configured to produce an electronic signal based on a detected force, acceleration, or pressure.

In some examples, heart sound input circuit 106 can be an electronic circuit or series of circuits configured to receive, modify, and transmit signals supplied by heart sound sensor 104. In some examples, combination circuit 108 can be an electronic circuit or series of circuits configured to receive and process signals received from heart sound input circuit 106. In some examples, combination circuit 108 can be configured to perform multiple operations (or calculations) on or using the signals received from heart sound input circuit 106.

In operation of one example, heart sound sensor 104 can detect heart sound information of a heart of patient 101 over one or more physiologic intervals that include at least a portion of a cardiac cycle. Heart sound sensor 104 can then transmit one or more signals containing heart sound information to heart sound input circuit 106. Heart sound input circuit 106 can modify the one or more signals containing heart sound information, in some examples, and can transmit the signal(s) to combination circuit 108. Combination circuit 108 can perform analysis or operations on the signal or signals provided by heart sound input circuit 106 to produce a combined heart sound signal, as discussed below in further detail. In some examples, because heart sound detection of system 100 does not rely on electrical heart signals, the produced combined heart sound signal can be less susceptible to electric or electromagnetic interference.

Figure 1B:
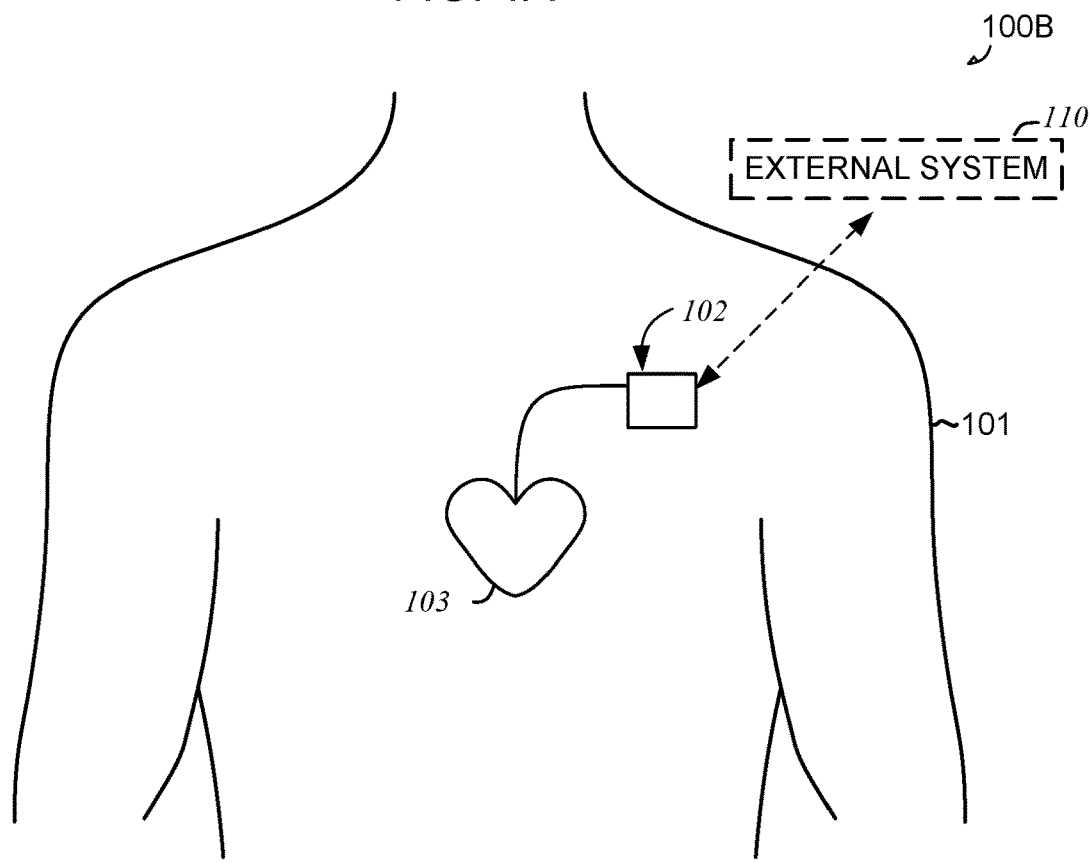

FIG. 1B illustrates a schematic view of system 100B including device 102 configured to detect heart sound information of heart 103 of patient 101, and external system 110.

In some examples, external system 110 can be a device located external to patient 101, such as in a portable computer, wearable device, or other device station. External system 110 can include one or more of the components of device 102, such as heart sound sensor 104, heart sound input circuit 106, and combination circuit 108. In some examples, external system 110 can be in wired or wireless communication with device 102, depending on system design and requirements.

FIGS. 2A-2D illustrate graphs of example signals including heart sound information detected over a physiologic interval and an example combined heart sound signal over the physiologic interval.

Figure 2C:
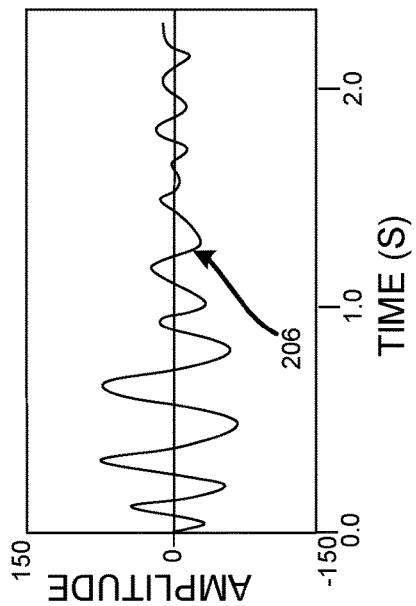
FIGS. 2A-2D illustrate graphs of example signals including heart sound information provided by an example system over a physiologic interval and an covariance signal over the physiologic interval.
Figure 2D:
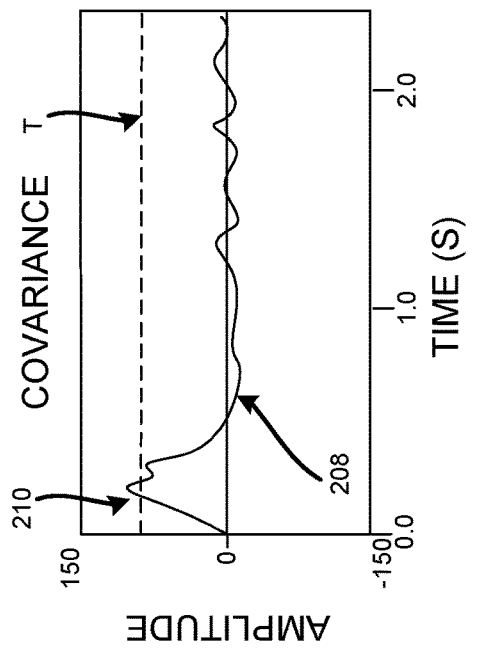
Figure 2A:
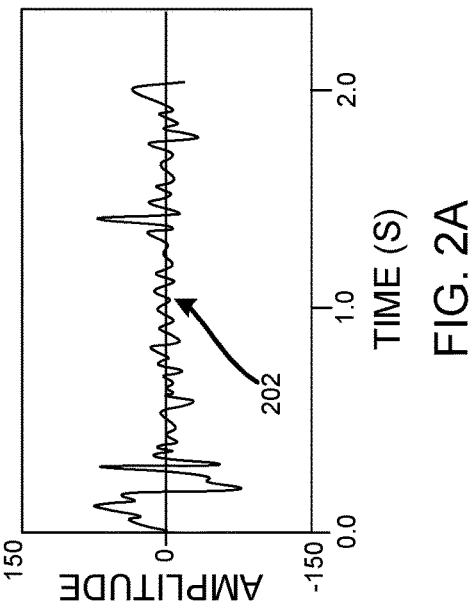
Figure 2B:
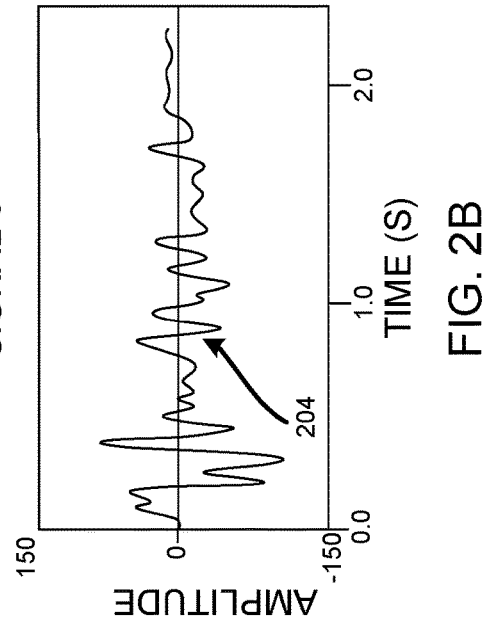

FIG. 2A illustrates signal 202 including heart sound information over a first physiologic interval. In an example, signal 202 can include heart sound information detected along a first axis. FIG. 2B illustrates signal 204 including heart sound information over a first physiologic interval. In an example, signal 204 can be include heart sound information detected along a second axis. FIG. 2C illustrates signal 206 including heart sound information over a first physiologic interval. In an example, signal 206 can include heart sound information detected along a third axis. FIG. 2D illustrates covariance 208 that can be calculated by using a covariance of signals 202 and 204, in some examples. In other examples, covariance 208 can be calculated by using a covariance of signals 202, 204, and 206.

In an example, an input circuit and a combination circuit, such as input circuit 106 and combination circuit 108 of FIG. 1, can combine signals 202, and/or 204, and/or 206 to produce a combined heart sound signal. In one example, shown in FIG. 2D, the covariance 208 of signals 202, 204, and 206 can be determined. Covariance 208 can then be used to detect specific heart sound fiducials (e.g. S1, S2, S3, etc.). The identified fiducial can then be used to align signals 202, 204, and 206 to produce a combined heart sound signal. In another example, one or more of signals 202, 204, and 206 can be aligned to maximize or minimize the covariance 208. In other examples, one or more of adding, subtracting, multiplying, differentiating, and integrating signals 202, 204, and/or 206 can be used to align signals 202, 204, and/or 206 to produce the combined heart sound signal.

In one example, peak amplitudes of covariance 208 (e.g., beyond a predetermined threshold) can indicate the presence of a specific heart sound fiducial (or other fiducial) within covariance 208. For example, if peak 210 is beyond a threshold T, a specific heart sound fiducial can be detected at peak 210 of covariance 208. The timestamp of peak 210 can be used to align signals 202, 204, and/or 206 to produce the combined heart sound signal. Once signals 202, 204, and/or 206 are aligned, they can be combined in many ways. For example, signals 202, 204, and/or 206 can be combined by averaging signals 202, 204, and/or 206, by using weighted averages of signals 202, 204, and/or 206 (such as based on signal-to-noise ratio), and any one of signals 202, 204, and 206 can be used to amplify another of signals 202, 204, and 206.

In other examples, the timestamp of peak 210 can be used to detect additional heart sounds or fiducials within covariance 208 (e.g., S2, S3, S4, etc.), or one or more heart sounds or fiducials in a subsequent physiologic interval. In other examples, peak 210 (or additional fiducials in this or other physiologic intervals) can be used to select the beginning and end of physiologic intervals, or instance windows, within the covariance 208. Instance windows of covariance 208 can be used to align signals 204, 206, and 208, and can also be used to average combined signals over different physiologic intervals. In each case, the combined heart sound signal can have a relatively low signal-to-noise ratio.

Figure 3:
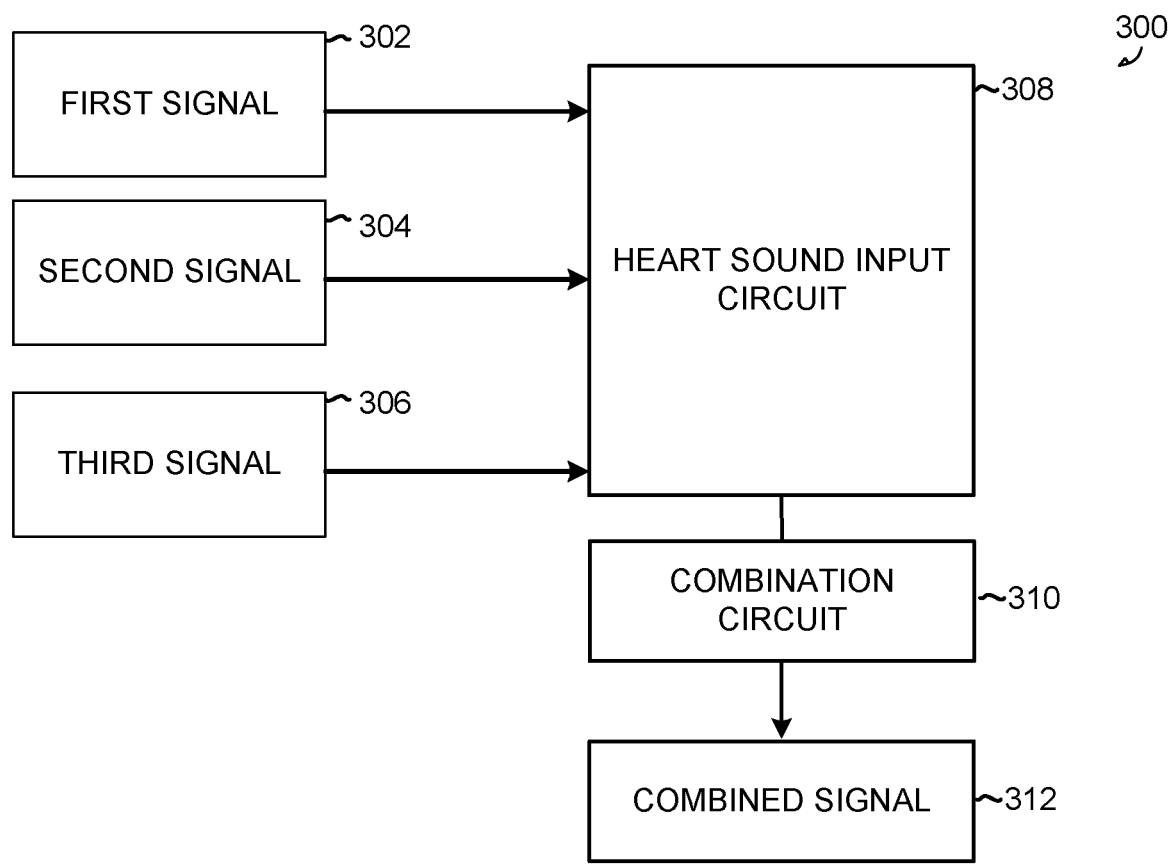
FIG. 3 illustrates a schematic view of an example system including a heart sound input circuit and a combination circuit.

FIG. 3 illustrates a schematic view of example system 300 including heart sound input circuit 308 and combination circuit 310. FIG. 3 illustrates first signal 302, second signal 304, and third signal 306, Heart sound input circuit 308 can receive first signal 302, second signal 304, and third signal 306, in some examples. Heart sound input circuit 308 can provide one or more of first signal 302, second signal 304, and third signal 306 to combination circuit 310 for further modification and/or analysis. In some examples, heart sound input circuit 308 can modify one or more of first signal 302, second signal 304, and third signal 306 before providing the signals to combination circuit 310. Combination circuit 310 can use these signals to produce combined heart sound signal 312.

In some examples, a heart sound sensor, such as heart sound sensor 104 of FIG. 1, can produce each of first signal 302, second signal 304, and third signal 306. In one example, a heart sound sensor can produce first signal 302, where first signal 302 can include heart sound information detected along a first axis. In the same example, the heart sound sensor can produce second signal 304, where second signal 304 can include heart sound information taken along a second axis different than the first axis. In this example, a single heart sound sensor can produce first signal 302 and second signal 304 by detecting heart sound information along multiple, different axes. In another example, multiple, single-axis sensors can produce first signal 302 and second signal 304.

In either of these examples, heart sound input circuit 308 can receive first signal 302 and second signal 304, which can provide first signal 302 and second signal 304 to combination circuit 310. Combination circuit 310 can then combine first signal 302 and second signal 304 to produce combined heart sound signal 312. Combination circuit 310 can create the combined heart sound signal in many ways using first signal 302 and second signal 304.

In one example, combination circuit 310 can use the covariance of first signal 302 and second signal 304 to detect one or more fiducials or other markers to align first signal 302 and second signal 304, and to produce combined signal 312, such as by averaging or otherwise combining the aligned signals.

In other examples (or additionally), combination circuit 310 can produce combined heart sound signal 312 by aligning the signals using one or more of adding, subtracting, multiplying, differentiating, and integrating first signal 302 and second signal 304.

In other examples, combination circuit 310 can use first signal 302, second signal 304, and third signal 306 to produce combined heart sound signal 312. In an example, a single sensor can produce first signal 302 based on detected heart sound information along a first axis, second signal 304 based on detected heart sound information along a second axis different than the first axis, and third signal 306 based on detected heart sound information along a third axis different than the first and second axes.

In other examples, multiple sensors can be used to produce first signal 302, second signal 304, and third signal 306. For example, a first sensor can produce first signal 302 based on detected heart sound information along a first axis, a second sensor can produced second signal 304 based on detected heart sound information along a second axis different than the first axis, and a third sensor can produce third signal 306 based on detected heart sound information along a third axis different than the first and second axes.

In another example, first, second, and third signals 302, 304, and 306 can be aligned over different physiological intervals. For example, first signal 302 from a first physiologic interval can be aligned with first signal 302 from a second physiologic interval. Second signal 304 and third signal 306 can similarly be aligned. After alignment, first, second, and third signals 302, 304, and 306 from the first physiologic interval can be combined.

In another example, all of first, second, and third signals 302, 304, and 306 of a first physiologic interval can be aligned together with first, second, and third signals 302, 304, and 306 over a second physiologic interval prior to combination. In yet another example, first, second, and third signals 302, 304, and 306 can all be from different physiologic intervals and can be aligned prior to combination with first, second, and third signals 302, 304, and 306 all from the same or different physiologic intervals.

In either of these examples, combination circuit 310 can create combined heart sound signal 312 in many ways using first signal 302, second signal 304, and third signal 306. For example, combination circuit 310 can use the covariance of first signal 302, second signal 304, and third signal 306 to align first signal 302, second signal 304, and third signal 306. Once aligned, combination circuit 310 can combine the aligned first, second, and third signals 302, 304, and 306, for example, by averaging the signals, to create combined heart sound signal 312. In other examples (or additionally), combination circuit 310 can determine alignment of the first, second, and third signals 302, 304, and 306 using one or more of adding, subtracting, multiplying, differentiating, and integrating first signal 302, second signal 304, and third signal 306.

In another example, combination circuit 310 can use only first signal 302 to produce combined heart sound signal 312. In this example, heart sound input circuit 308 can receive only first signal 302, which can include heart sound information over a physiologic interval. In other examples, heart sound input circuit 308 can receive multiple signals and select only one signal to be delivered to combination circuit 310. In this example, heart sound circuit 308 can provide to combination circuit 310 a first signal including a first portion of the heart sound information and a second signal including a different second portion of the heart sound information. Combination circuit 310 can then produce combined heart sound signal 312 over the physiologic interval using the first portion signal and the second portion signal.

In one example, heart sound input circuit 308 can be configured to split first signal 302 into the first and second signals. In this example, first signal 302 can be split such that the two signals have either a non-overlapping range of frequencies or an overlapping range of frequencies. In another example, heart sound input circuit 308 can be configured to filter first signal 302 into the first and second signals, where the first filtered signal has a different range of frequencies than the second filtered signal. In some examples, frequency bands can be split between 2-20 Hz bands and 20-50 Hz bands. In one example, frequency splitting of first signal 302 can be performed using wavelet transform.

In any of the examples discussed above, the combined heart sound signal, an averaged combined heart sound signal, or a combined heart sound signal ensemble over multiple physiologic intervals can be used to detect S1, S2 S3, or a calculation of one or more windows or markers used to detect or determine S3 (e.g., using S2 timing, etc.). These methods, devices, and systems can therefore be used to detect heart sounds over one or more physiologic intervals and can be used to produce a combined heart sound signal without the aid of a detected R wave or other marker or fiducial of an electrical signal of the heart. Because an R wave signal is not required to produce a combined heart sound signal, electrical error and electromagnetic interference can be reduced. Additionally, by using multiple signals to create a combined heart sound signal, signal-to-noise ratio of the combined heart sound signal can be reduced relative to use of a single signal R wave signal or a single signal including heart sound information.

In other examples, more sensors can be used. For example, two multi-axis sensors can be used and multiple combined heart sound signals can be averaged or compared and the better signal selected. Alternatively two single-axis sensors can be used at each axis and the single-axis signals can be averaged (or the better signal selected) prior to combination.

In another example, R wave detection can be used in conjunction with direct heart sound detection. In this example, the combined heart sound signal (or averaged combined heart sound signal) can be compared to an R wave signal (or averaged R wave signal) where the better signal can be selected based on noise levels to improve overall averaging process. In some examples, an automatic selection of the best detection method can be based on feedback such as signal-to-noise ratio.

In yet another example, each or any of first signal 302, second signal 304, and third signal 306 can be separated using wavelet transform. The separated signals can be used to align the signals, and/or can be combined to create combined heart sound signal 312 using combination circuit 310.

Figure 4:
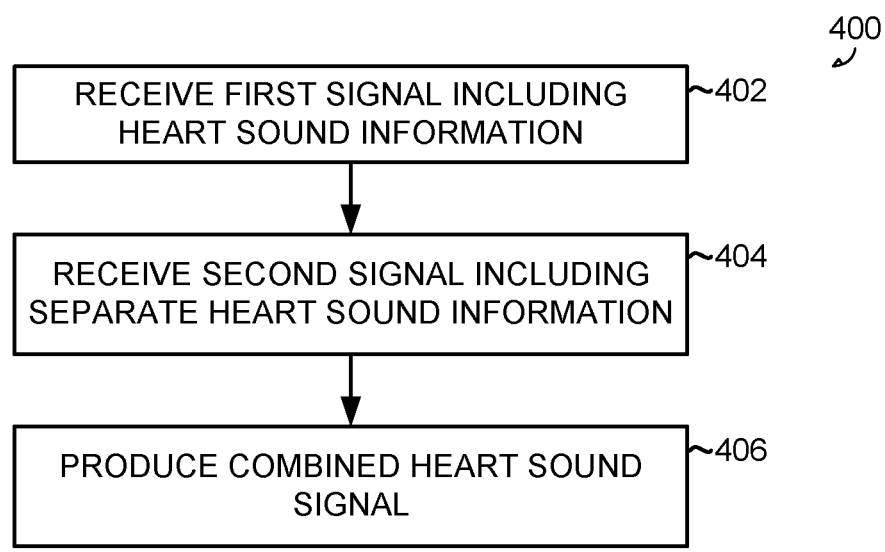
FIG. 4 illustrates an example method of producing a combined heart sound signal.

FIG. 4 illustrates an example method 400 of producing a combined heart sound signal. The steps or operations of method 400 are illustrated in a particular order for convenience and clarity; some of the discussed operations can be performed in a different sequence or in parallel without materially impacting other operations.

At step 402, a first signal including heart sound information over a first physiologic interval can be received, such as using a heart sound input circuit (e.g., heart sound input circuit 308 of FIG. 3, etc.). At step 404, a second signal including heart sound information over the first physiologic interval can be received, such as using the heart sound input circuit. In an example, a heart sound sensor, such as heart sound sensor 104 of FIG. 1, can produce the first and second signals including heart sound information. In other examples, the second signal including heart sound information can be produced by a second, different heart sound sensor. At step 406 a combination circuit, such as combination circuit 310 of FIG. 3, can be used to produce a combined heart sound signal over the first physiologic interval using the first and second signals. In one example, the combination circuit can align the first and second signals using a covariance of the first and second signals to produce the combined heart sound signal.

In another example, a third signal can include heart sound information over the first physiologic interval. The third signal can be produced by the heart sound sensor, or by a third, different heart sound sensor, and received by the heart sound input circuit. The combined heart sound signal can be produced using the first, second, and third signals. Additionally, the combination circuit can align the first, second, and third signals using a covariance of the first, second, and third signals to produce the combined heart sound signal.

In another example, the first signal can include heart sound information detected along a first axis and the second signal can include heart sound information detected along a second axis that is different from the first axis. In yet another example, a third signal can be produced as a function of heart sound information detected over the first physiologic interval using the heart sound sensor. In some of these examples, the third signal can include heart sound information over the first physiologic interval along a third axis.

Figure 5:
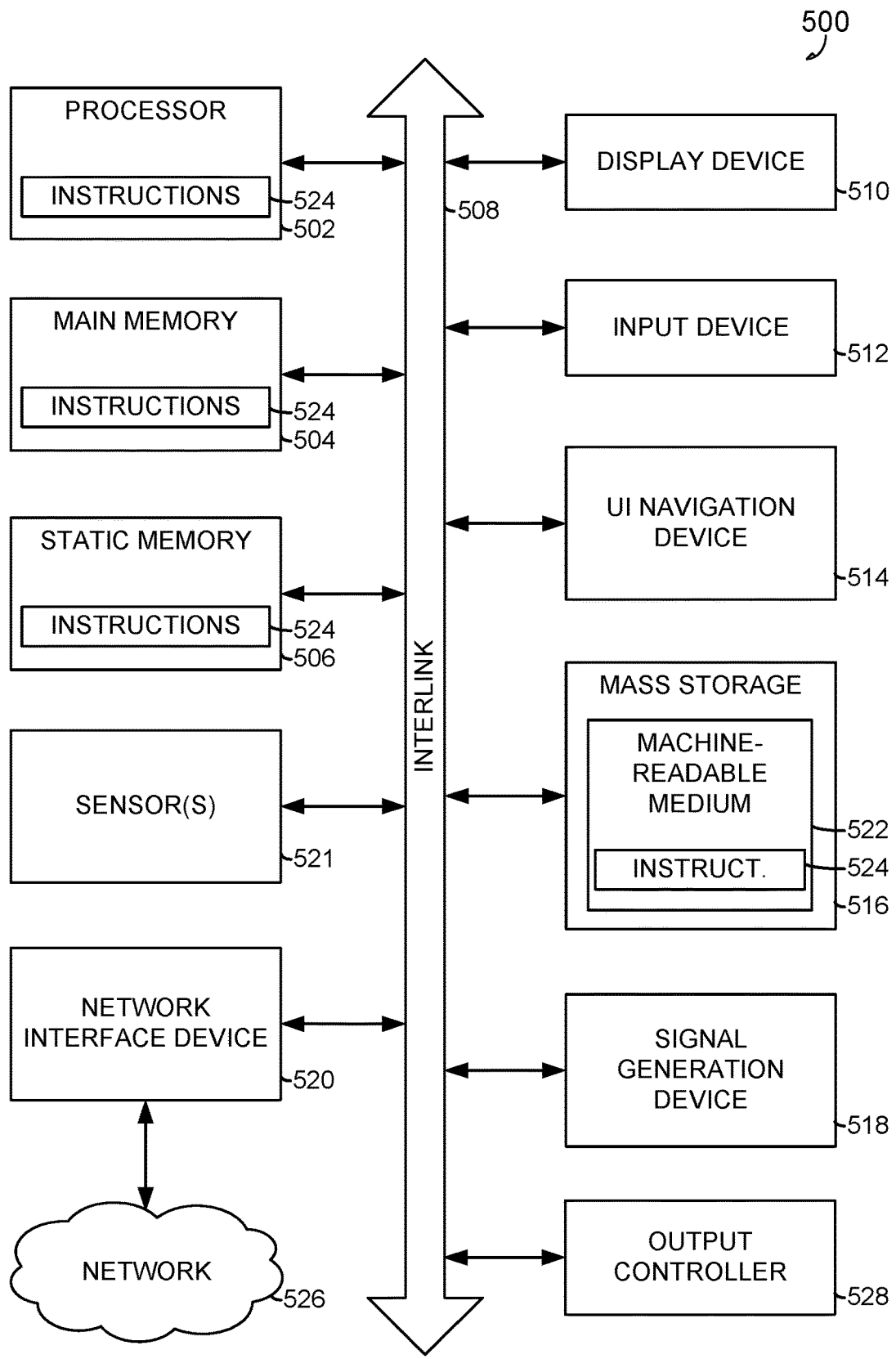
FIG. 5 illustrates a block diagram of an example machine upon which any one or more of the techniques (e.g., methodologies) discussed herein may perform.

FIG. 5 illustrates a block diagram of an example machine 500 upon which any one or more of the techniques (e.g., methodologies) discussed herein may perform. Portions of this description may apply to the computing framework of various portions of the LCP device, the IMD, or the external programmer.

In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation.

Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 500 may further include a display unit 510 (e.g., a raster display, vector display, holographic display, etc.), an alphanumeric input device 512 (e.g., a keyboard), and a user interface (UI) navigation device 514 (e.g., a mouse). In an example, the display unit 510, input device 512 and UI navigation device 614 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system comprising:
    a heart sound input circuit configured to:
        receive a first signal including heart sound information over a first physiologic interval; and
        receive a second signal including heart sound information over the first physiologic interval; and
    a combination circuit configured to produce a combined heart sound signal over the first physiologic interval using the first and second signals,
    wherein the combination circuit is configured to align the first and second signals using a covariance of the first and second signals, and to produce the combined heart sound signal using the aligned first and second signals.

2. The system of claim 1, wherein the combination circuit is configured to produce the combined heart sound signal using the first and second signals without reference to an electrical signal of the heart, and wherein the first physiologic interval includes at least a portion of a cardiac cycle.

3. The system of claim 1, wherein the first signal includes heart sound information detected along a first axis and the second signal includes heart sound information detected along a second axis, different from the first axis.

4. The system of claim 1, wherein the heart sound input circuit is configured to receive a third signal including heart sound information over the first physiologic interval, and wherein the combination circuit is configured to produce the combined heart sound signal using the first, second, and third signals.

5. The system of claim 1, further comprising:
    a heart sound sensor configured to detect heart sound information over the first physiologic interval, to produce the first signal as a function of heart sound information detected over the first physiologic interval, and to produce the second signal as a function of heart sound information detected over the first physiologic interval.

6. The system of claim 5, wherein the heart sound input circuit is configured to receive a third signal including heart sound information over the first physiologic interval, wherein the combination circuit is configured to produce the combined heart sound signal using the first, second, and third signals, and wherein the heart sound sensor is configured to produce the third signal as a function of heart sound information detected over the first physiologic interval.

7. A method comprising:
    receiving a first signal including heart sound information over a first physiologic interval using a heart sound input circuit;
    receiving a second signal including heart sound information over the first physiologic interval using the heart sound input circuit; and
    producing, using a combination circuit, a combined heart sound signal over the first physiologic interval using the first and second signals,
    wherein producing the combined heart sound signal includes aligning the first and second signals using a covariance of the first and second signals, and producing the combined heart sound signal using the aligned first and second signals.

8. The method of claim 7, wherein producing the combined heart sound signal is performed without reference to an electrical signal of the heart, and wherein the first physiologic interval includes at least a portion of a cardiac cycle.

9. The method of claim 7, wherein the first signal includes heart sound information detected along a first axis and the second signal includes heart sound information detected along a second axis, different from the first axis.

10. The method of claim 9, further comprising:
    providing the first signal and the second signal using a multi-axis heart sound sensor.

11. The method of claim 7, further comprising:
    receiving a third signal including heart sound information over the first physiologic interval using the heart sound input circuit, wherein producing the combined heart sound signal over the first physiologic interval includes using the first, second, and third signals.

12. The method of claim 7, further comprising:
    detecting heart sound information over the first physiologic interval using a heart sound sensor; and
    producing the first signal as a function of heart sound information detected over the first physiologic interval and the second signal as a function of heart sound information detected over the first physiologic interval using the heart sound sensor.

13. The method of claim 12, further comprising:

receiving a third signal including heart sound information over the first physiologic interval using the heart sound input circuit, wherein producing the combined heart sound signal over the first physiologic interval includes using the first, second, and third signals; and producing the third signal as a function of heart sound information detected over the first physiologic interval using the heart sound sensor.

14. A system comprising:

a heart sound input circuit configured to receive a single signal including heart sound information and to provide a first signal including a first portion of the heart sound information and a second signal including a different second portion of the heart sound information; and a combination circuit configured to produce a combined heart sound signal over the first physiologic interval using the first and second signals, wherein the heart sound input circuit is configured to split the single signal into the first and second signals, and wherein the heart sound input circuit is configured to filter the single signal into the first and second signals, the first signal having a different range of frequencies than the second signal.

15. The system of claim 14, wherein the combination circuit is configured to produce the combined heart sound signal using the first and second signals without reference to an electrical signal of the heart.

16. The system of claim 14, wherein the combination circuit is configured to align the first and second signals using a covariance of the first and second signals, and to produce the combined heart sound signal using the aligned first and second signals.

* * * * *